United States Patent
Liu et al.

(10) Patent No.: US 8,396,188 B2
(45) Date of Patent: Mar. 12, 2013

(54) X-RAY SYSTEM AND METHOD FOR PRODUCING X-RAY IMAGE DATA

(75) Inventors: James Zhengshe Liu, Glenview, IL (US); Paul Richard Granfors, Berkeley, CA (US); Kenneth Scott Kump, Waukesha, WI (US); Ping Xue, Pewaukee, WI (US); Donald Fayette Langler, Brookfield, WI (US); Brian John Kost, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 233 days.

(21) Appl. No.: 13/011,016

(22) Filed: Jan. 21, 2011

(65) Prior Publication Data
US 2012/0189099 A1 Jul. 26, 2012

(51) Int. Cl.
*G01N 23/04* (2006.01)

(52) U.S. Cl. .......................................... 378/62; 378/98.8

(58) Field of Classification Search ............... 378/62, 378/98.8, 98.12, 204, 210; 382/132
See application file for complete search history.

(56) References Cited

U.S. PATENT DOCUMENTS

| | | | |
|---|---|---|---|
| 5,687,717 A | 11/1997 | Halpern et al. | |
| 6,475,146 B1 | 11/2002 | Frelburger et al. | |
| 7,006,600 B1 | 2/2006 | Krema et al. | |
| 7,038,588 B2 | 5/2006 | Boone et al. | |
| 7,343,565 B2 | 3/2008 | Ying et al. | |
| 7,502,445 B2 | 3/2009 | Shi et al. | |
| 7,549,961 B1 | 6/2009 | Hwang | |
| 7,755,059 B2 | 7/2010 | Liu et al. | |
| 7,873,145 B2 | 1/2011 | Liu et al. | |
| 2002/0150214 A1 | 10/2002 | Spahn | |
| 2003/0169850 A1 | 9/2003 | Kump et al. | |
| 2004/0086077 A1 | 5/2004 | Moriyama | |
| 2005/0265267 A1 | 12/2005 | Hwang | |
| 2007/0116180 A1 | 5/2007 | Omernick et al. | |
| 2007/0189462 A1 | 8/2007 | Spahn | |
| 2008/0240358 A1 | 10/2008 | Utschig et al. | |
| 2010/0019176 A1 | 1/2010 | Tanabe | |
| 2010/0104066 A1 | 4/2010 | Foos et al. | |
| 2010/0108898 A1 | 5/2010 | Zhang et al. | |
| 2010/0111263 A1 | 5/2010 | Lamberty et al. | |
| 2010/0246757 A1 | 9/2010 | Liu et al. | |

FOREIGN PATENT DOCUMENTS

FR 2914433 A1 10/2008

OTHER PUBLICATIONS

U.S. Appl. No. 13/010,982, filed Jan. 21, 2011, Liu et al.
U.S. Appl. No. 13/011,033, filed Jan. 21, 2011, Liu et al.
Search Report and Written Opinion from corresponding PCT Application No. PCT/US2012/021962 Apr. 4, 2012.
Search Report and Written Opinion from corresponding PCT Application No. PCT/US2012/021981 May 23, 2012.

*Primary Examiner* — Jurie Yun
(74) *Attorney, Agent, or Firm* — Fletcher Yoder, P.C.

(57) ABSTRACT

An X-ray imaging method includes performing an X-ray exposure via an X-ray radiation source responsive to a source controller. The method also includes sampling X-ray image data via a digital detector without communication of timing signals from the source controller. The method further includes combining the sampled X-ray image data of at least one imaging frame or two or more imaging frames with at least one of the frames spanning a duration in which the exposure occurred, to produce X-ray image data capable of being reconstructed into a user-viewable image.

39 Claims, 10 Drawing Sheets

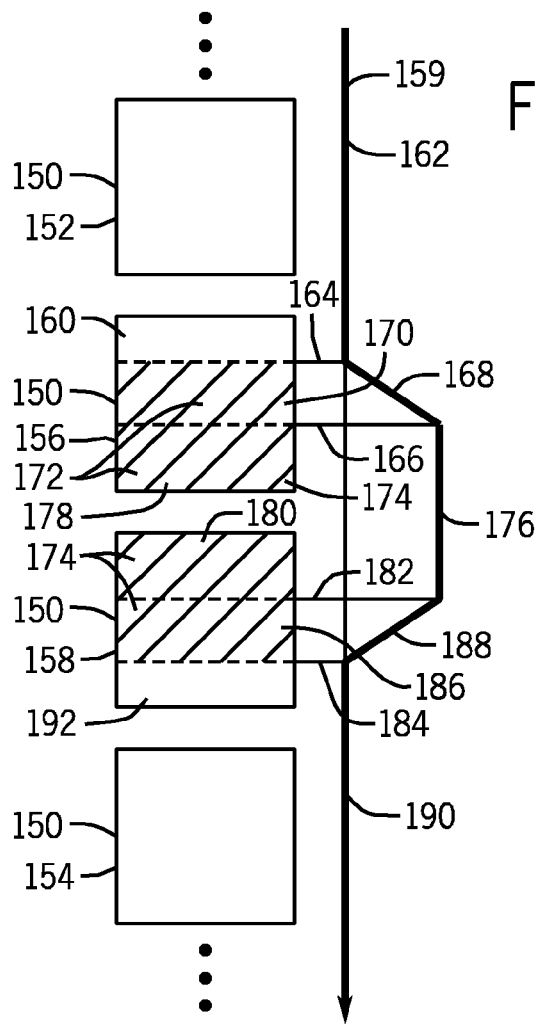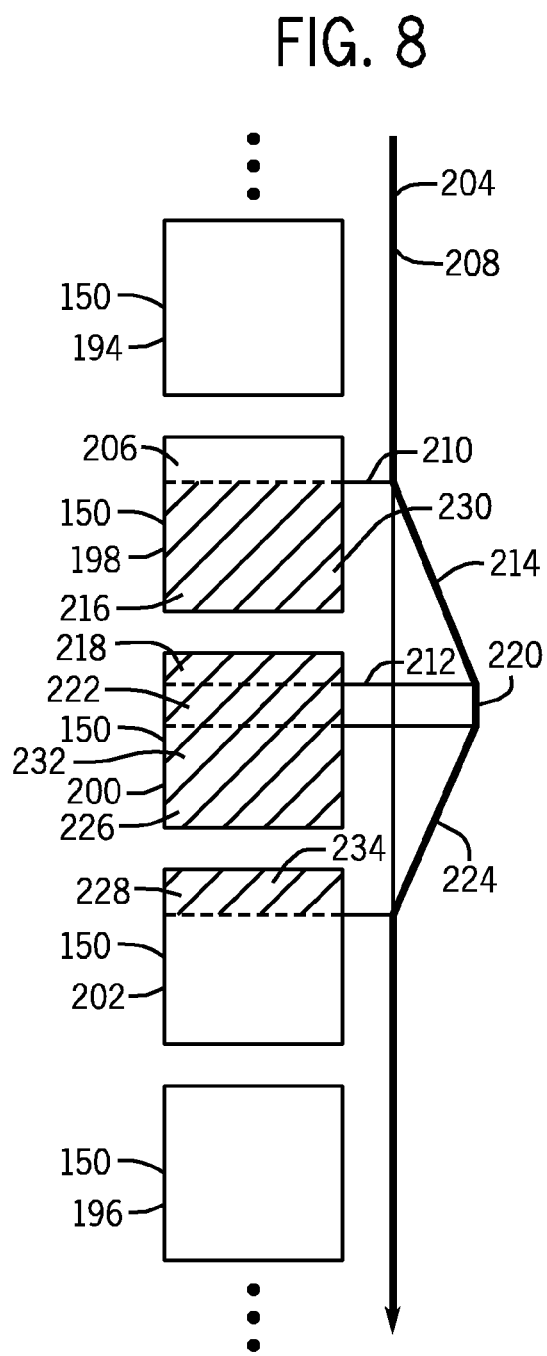

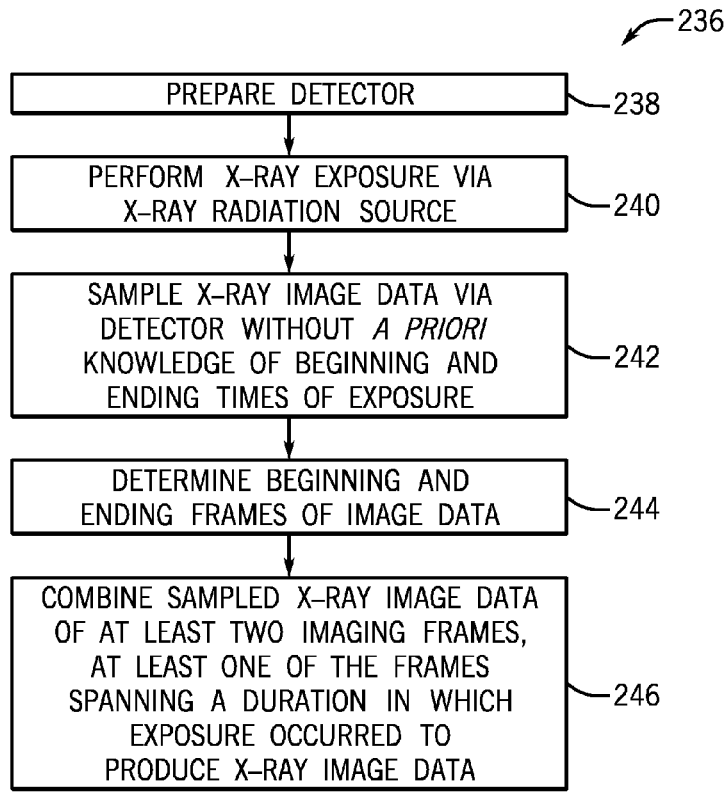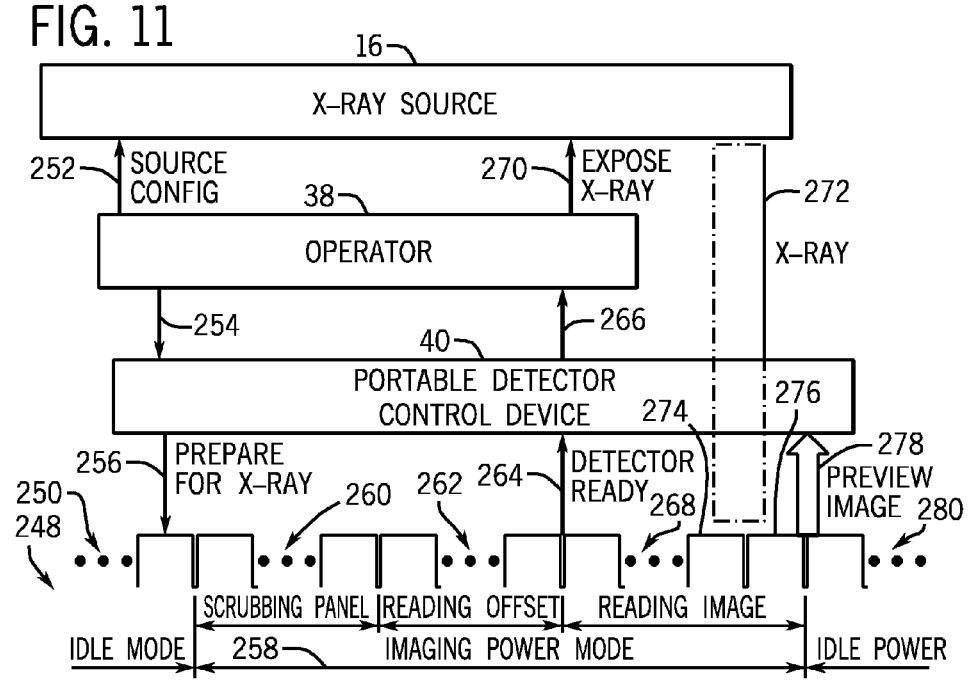

X-RAY SYSTEM AND METHOD FOR PRODUCING X-RAY IMAGE DATA

BACKGROUND OF THE INVENTION

The subject matter disclosed herein relates to X-ray imaging systems and more particularly to X-ray imaging system using digital detectors.

The advent of digital X-ray detectors has brought enhanced workflow and high image quality to medical imaging. However, many of the earlier radiographic imaging systems employ conventional X-ray imaging using film and/or computed radiography. In order to obtain images from these systems, the imaging medium must be transported and processed after each exposure, resulting in a time delay in obtaining the desired images. Digital radiography provides an alternative that allows the acquisition of image data and reconstructed images on the spot for quicker viewing and diagnosis. However, the cost of replacing the earlier conventional radiographic imagining systems with digital radiographic imaging systems may be imposing to a hospital or tertiary care medical center. Hence, the need to retrofit the earlier radiographic imaging systems for digital radiography in a cost effective manner involving as few components of the systems as possible.

BRIEF DESCRIPTION OF THE INVENTION

In accordance with one embodiment, an X-ray imaging method includes performing an X-ray exposure via an X-ray radiation source responsive to a source controller. The method also includes sampling X-ray image data via a digital detector without communication of timing signals from the source controller. The method further includes combining the sampled X-ray image data of at least one imaging frame or two or more imaging frames with at least one of the frames spanning a duration in which the exposure occurred, to produce X-ray image data capable of being reconstructed into a user-viewable image.

In accordance with another embodiment, an X-ray imaging method includes performing an X-ray exposure via an X-ray radiation source. The method also includes sampling X-ray image data via a digital detector without a priori knowledge of beginning and ending times of the X-ray exposure. The method further includes determining beginning and ending frames of the X-ray image data. The method yet further includes combining the sampled X-ray image data of at least one imaging frame or two or more imaging frames with at least one of the frames spanning a duration in which the exposure occurred, to produce X-ray image data capable of being reconstructed into a user-viewable image.

In accordance with a further embodiment, the X-ray imaging system includes an X-ray radiation source, a source controller coupled to the source and configured to command X-ray emission of X-rays for image exposures, and a digital X-ray detector configured to sample X-ray image data without communication from the source controller. The system also includes a portable detector control device configured to communicate instructions to the detector for acquisition of the X-ray image data and to receive the X-ray image data from the detector for processing and preview. At least one of the detector, the portable detector control device, and a processing system in communication with the detector and/or the portable detector control device is configured to combine the sampled X-ray image data of at least one imaging frame or two or more imaging frames with at least one of the frames spanning a duration in which the exposure occurred, to produce X-ray image data capable of being reconstructed into a user-viewable image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 7 is a diagrammatical representation of sampling X-ray image data from two imaging frames, in accordance with aspects of the present technique;

FIG. 8 is a diagrammatical representation of sampling and combining X-ray image data from three imaging frames, in accordance with aspects of the present technique;

FIG. 10 is a flow diagram of a method for sampling and combining X-ray image data to produce X-ray image data capable of being reconstructed into a user-viewable image, in accordance with aspects of the present technique;

FIG. 11 is a diagrammatical representation of workflow during an acquisition sequence in which both image data and offset data are acquired for producing user-viewable images, in accordance with aspects of the present technique;

DETAILED DESCRIPTION OF THE INVENTION

Figure 1:
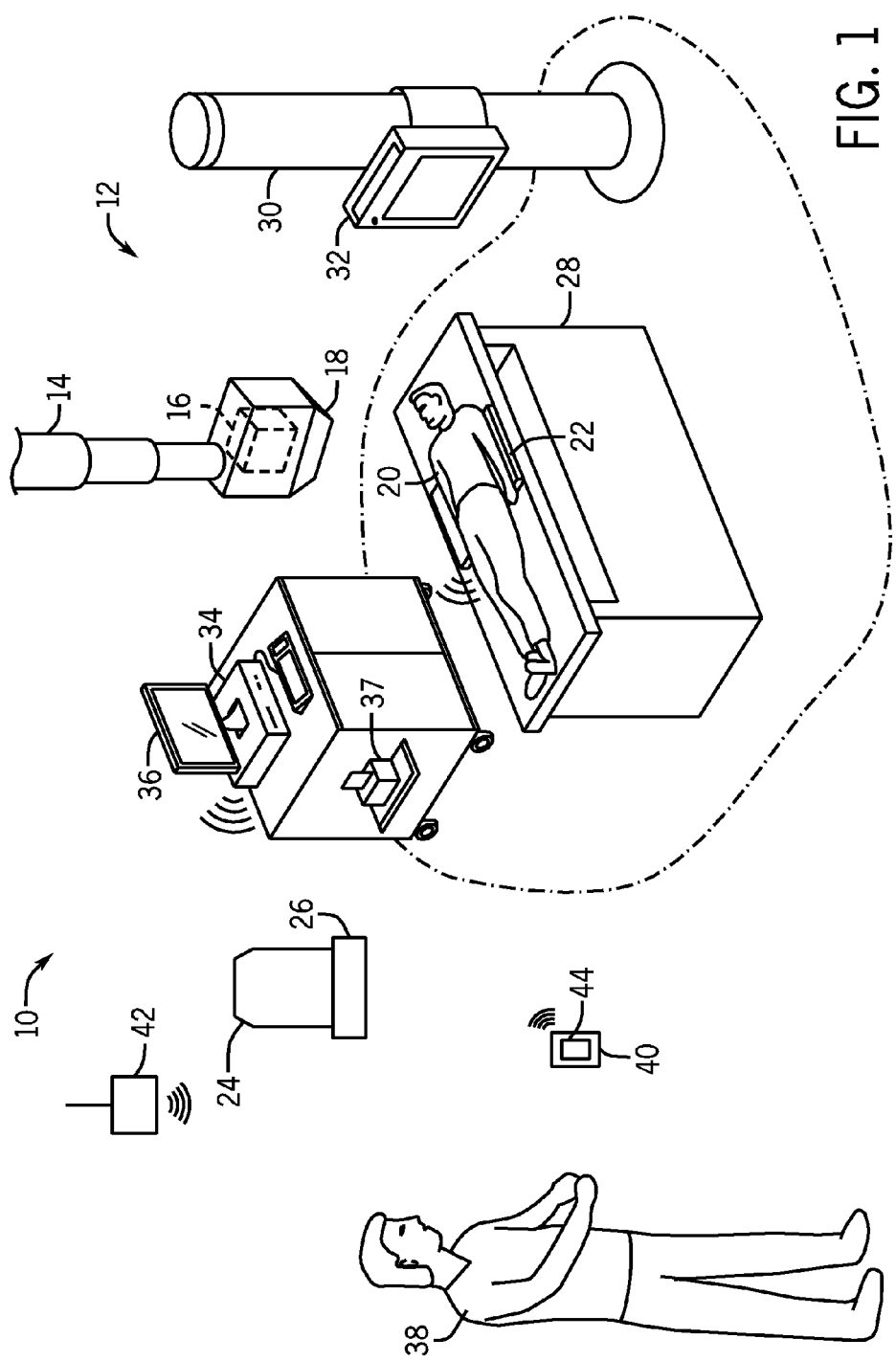
FIG. 1 is a perspective view of an exemplary fixed X-ray system, equipped in accordance with aspects of the present technique.

Referring generally to FIG. 1, an X-ray system is represented, referenced generally by reference numeral 10. In the illustrated embodiment, the X-ray system 10, as adapted, is a digital X-ray system. The X-ray system 10 is designed both to acquire image data and to process the image data for display in accordance with the present technique. Throughout the following discussion, however, while basic and background information is provided on the digital X-ray system used in medical diagnostic applications, it should be born in mind that aspects of the present techniques may be applied to digital detectors, including X-ray detectors, used in different settings (e.g., projection X-ray, computed tomography imaging, tomosynthesis imaging, etc.) and for different purposes (e.g., parcel, baggage, vehicle and part inspection, etc.).

In the embodiment illustrated in FIG. 1, the X-ray system 10 includes an imaging system 12. The imaging system 12 may be a conventional analog imaging system, retrofitted for digital image data acquisition and processing as described below. In one embodiment, the imaging system 12 may be a stationary system disposed in a fixed X-ray imaging room, such as that generally depicted in and described below with respect to FIG. 1. It will be appreciated, however, that the presently disclosed techniques may also be employed with other imaging systems, including mobile X-ray units and systems in other embodiments. The imaging system 12 includes an overhead tube support arm 14 for positioning a radiation source 16, such as an X-ray tube, and a collimator 18 with respect to a patient 20 and a detector 22. The detector 22 includes a digital X-ray detector. In some embodiments, the detector 22 may be selected from a plurality of detectors 22, represented by detector 24, from a dock 26 (e.g., charging dock). Each detector 22 of the plurality of detectors 22 may be labeled and designed for a particular type of imaging (e.g., fluoroscopic and radiographic imaging). The detector 22 is configured to acquire X-ray image data without communication from a controller of the X-ray radiation source 16. In other words, the detector 22 is without communication of timing signals from the controller of the source 16 as to an X-ray exposure. As a result, in preparation for acquiring X-ray image data the detector 22 is configured to continuously sample data prior to and during an X-ray exposure. Also, the detector 22 is configured to combine multiple frames that include imaging data to generate X-ray images. In addition, the detector 22 is configured to at least partially process X-ray image data.

In one embodiment, the imaging system 12 may be used in consort with one or both of a patient table 28 and a wall stand 30 to facilitate image acquisition. Particularly, the table 28 and the wall stand 30 may be configured to receive detector 22. For instance, detector 22 may be placed on an upper, lower or intermediate surface of the table 28, and the patient 20 (more specifically, an anatomy of interest of the patient 20) may be positioned on the table 28 between the detector 22 and the radiation source 16. Also, the wall stand 30 may include a receiving structure 32 also adapted to receive the detector 22, and the patient 20 may be positioned adjacent the wall stand 30 to enable the image data to be acquired via the detector 22. The receiving structure 32 may be moved vertically along the wall stand 30.

Also depicted in FIG. 1, the imaging system 12 includes a workstation 34, display 36, and printer 37. In one embodiment, the workstation 34 may include or provide the functionality of the imaging system 12 such that a user 38, by interacting with the workstation 34 may control operation of the source 16 and detector 22. In other embodiments, the functions of the imaging system 12 may be decentralized, such that some functions of the imaging system 12 are performed at the workstation 34 (e.g., controlling operation of the source 16, while other functions (e.g., controlling operation of the detector 22) are performed by another component of the X-ray system 10, such as a portable detector control device 40. The portable detector control device 40 may include a personal digital assistant (PDA), palmtop computer, laptop computer, smart telephone, tablet computer such as an iPad™, or any suitable general purpose or dedicated portable interface device. The portable detector control device 40 is configured to be held by the user 38 and to communicate wirelessly with the detector 22. It is noted that the detector 22 and portable detector control device 40 may utilize any suitable wireless communication protocol, such as an IEEE 802.15.4 protocol, an ultra wideband (UWB) communication standard, a Bluetooth communication standard, or any IEEE 802.11 communication standard. Alternatively, the portable detector control device may be configured to be tethered or detachably tethered to the detector 22 to communicate via a wired connection.

The portable detector control device 40 is also configured to communicate instructions (e.g., detector operating mode) to the detector 22 for the acquisition of X-ray image data. In turn, the detector 22 is configured to prepare for an X-ray exposure in response to instructions from the portable detector control device 40, and to transmit a detector ready signal to the device 40 indicating that the detector 22 is prepared to receive the X-ray exposure. The device 40 may also be configured to communicate patient information or X-ray technique information to the detector 22. Similar to the detector 22, the device 40 may be without communication from the controller of the X-ray source 16. Further, the portable detector control device 40 is configured to receive X-ray image data from the detector 22 for processing and image reconstruction. Indeed, both the detector 22 and the portable detector control device 40 are configured to at least partially process the X-ray image data. However, in certain embodiments, the detector 22 and/or the portable detector control device 40 are configured to fully process the X-ray image data. Also, the detector 22 and/or the device 40 is configured to generate a DICOM compliant data file based upon the X-ray image data, patient information, and other information. Further, the detector 22 and/or the device 40 is configured to wirelessly transmit (or via a wired connection) processed X-ray image data (e.g., partially or fully processed X-ray image data) to an institution image review and storage system over a network 42. The institution image review and storage system may include a hospital information system (HIS), a radiology information system (RIS), and/or picture archiving communication system (PACS). In some embodiments, the institution image review and storage system may process the X-ray image data. In one embodiment, the workstation 34 may be configured to function as a server of instructions and/or content on a network 42 of the medical facility. The detector 22 and/or device 40 are also configured to transmit, via a wired or wireless connection, processed X-ray images to the printer 37 to generate a copy of the image.

The portable detector control device 40 includes a user-viewable screen 44 and is configured to display patient data and reconstructed X-ray images based upon X-ray image data on the screen 44. The screen 44 may include a touch-screen and/or input device (e.g., keyboard) configured to input data (e.g., patient data) and/or commands (e.g., to the detector). For example, the device 40 may be used to input patient information and other imaging related information (e.g., type of source 16, imaging parameters, etc.) to form a DICOM image header. In one embodiment, the patient information may be transferred from a patient database via a wireless or wired connection from the network or the workstation 34 to the device 40. The detector 22 and/or device may incorporate the information for the image header with the X-ray image to generate the DICOM compliant data file. Also, the device 40 may be used to navigate X-ray images displayed on the screen 44. Further, the device 40 may be used to modify the X-ray images, for example, by adding position markers (e.g., "L"/ "R" for left and right, respectively) onto the image. In one embodiment, metal markers may be placed on the detector 22 to generate position markers.

In one embodiment, the imaging system 12 may be a stationary system disposed in a fixed X-ray imaging room, such as that generally depicted in and described above with respect to FIG. 1. It will be appreciated, however, that the presently disclosed techniques may also be employed with other imaging systems, including mobile X-ray units and systems, in other embodiments.

Figure 2:
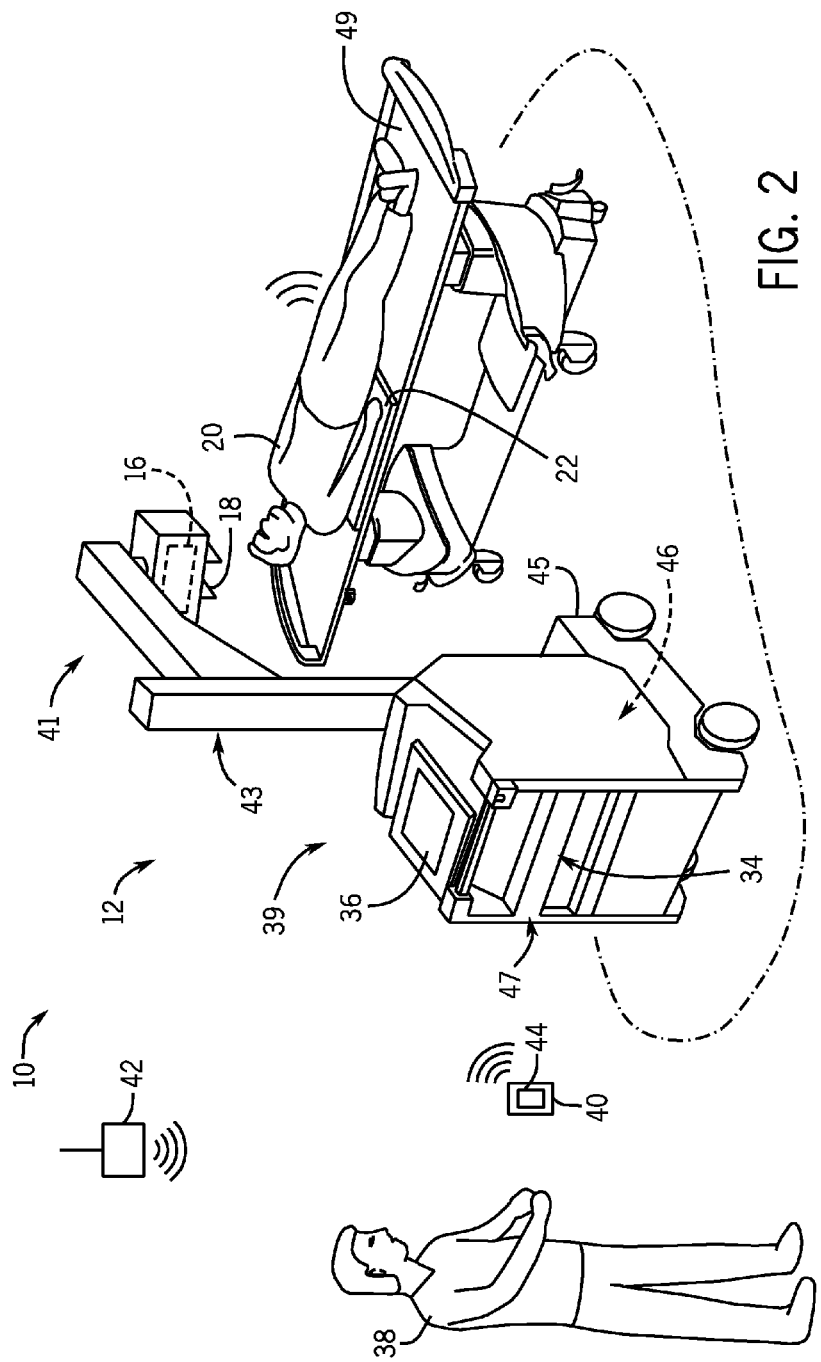
FIG. 2 is a perspective view of an exemplary mobile X-ray system, equipped in accordance with aspects of the present technique.

For instance, as illustrated in the X-ray system of FIG. 2, the imaging system 12 may be moved to a patient recovery room, an emergency room, a surgical room, or any other space to enable imaging of the patient 20 without requiring transport of the patient 20 to a dedicated (i.e., fixed) X-ray imaging room. The imaging system 12 includes a mobile X-ray base station 39 and detector 22. Similar to above, the imaging system 12 may be a conventional analog imaging system, retrofitted for digital image data acquisition and processing. In one embodiment, a support arm 41 may be vertically moved along a support column 43 to facilitate positioning of the radiation source 16 and collimator 18 with respect to the patient 20. Further, one or both of the support arm 41 and support column 43 may also be configured to allow rotation of the radiation source 16 about an axis. Further, the X-ray base station 39 has a wheeled base 45 for movement of the station 39. Systems electronic circuitry 46 with a base unit 47 both provides and controls power to the X-ray source 16 and the wheeled base 45 in the imaging system 12. The base unit 47 also has the operator workstation 34 and display 36 that enables the user 38 to operate the X-ray system 10. The operator workstation 34 may include buttons, switches, or the like to facilitate operation of the X-ray source 16. Similar to the X-ray system 10 in FIG. 1, the system 10 includes the portable control device 40. The detector 22 and portable control device 40 are as described above. In the X-ray system, the patient 20 may be located on a bed 49 (or gurney, table or any other support) between the X-ray source 16 and the detector 22 and subjected to X-rays that pass through the patient 20 and are received by the detector 22.

Figure 3:
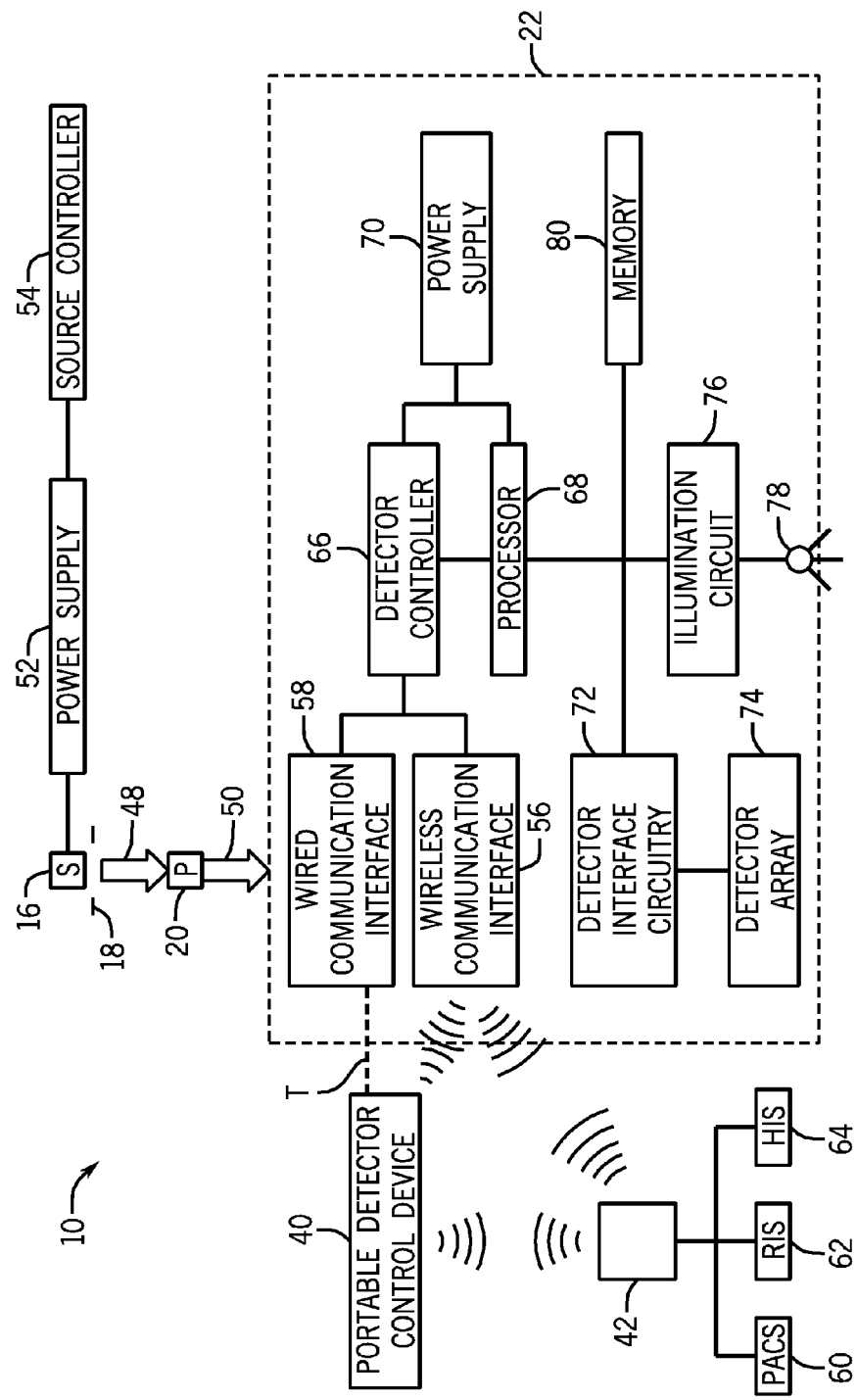
FIG. 3 is a diagrammatical overview of the X-ray system in FIGS. 1 and 2.

FIG. 3 is a diagrammatical overview of the X-ray system 10 in FIGS. 1 and 2 illustrating the components of the system 10 in more detail. The imaging system 10 includes the X-ray radiation source 16 positioned adjacent to a collimator 18. Collimator 18 permits a stream of radiation 48 to pass into a region in which a subject 20, such as a human patient 20, is positioned. A portion of the radiation 50 passes through or around the subject 20 and impacts the digital X-ray detector 22. As described more fully below, detector 22 converts the X-ray photons received on its surface to lower energy photons, and subsequently to electric signals which are acquired and processed to reconstruct an image of the features within the subject 20.

The source 16 is coupled to a power supply 52 which furnishes power for examination sequences. The source 16 and power supply 52 are coupled to a source controller 54 configured to command X-ray emission of X-rays for image exposures. As mentioned above, the detector 22 is configured to acquire X-ray image data without communication from the source controller 54. Instead, the detector 22 is responsive to the portable detector control device 40 configured to communicate instructions the detector 22 for acquisition of the X-ray image data. In addition, the portable detector control device 40 is configured to receive the X-ray image data from the detector 22 for processing and imaging reconstruction.

The detector 22 includes a wireless communication interface 56 for wireless communication with the device 40, as well as a wired communication interface 58, for communicating with the device 40 when it is tethered to the detector 22. The detector 22 and the device may also be in communication with the institution image review and storage system over the network 42 via a wired or wireless connection. As mentioned above, the institution image review and storage system may include PACS 60, RIS 62, and HIS 64. It is noted that the wireless communication interface 56 may utilize any suitable wireless communication protocol, such as an ultra wideband (UWB) communication standard, a Bluetooth communication standard, or any 802.11 communication standard. Moreover, detector 22 is coupled to a detector controller 66 which coordinates the control of the various detector functions. For example, detector controller 66 may execute various signal processing and filtration functions, such as for initial adjustment of dynamic ranges, interleaving of digital image data, and so forth. The detector controller 66 is responsive to signals from the device 40. The detector controller 66 is linked to a processor 68. The processor 68, the detector controller 66, and all of the circuitry receive power from a power supply 70. The power supply 70 may include one or more batteries.

Also, the processor 68 is linked to detector interface circuitry 72. The detector 22 converts X-ray photons received on its surface to lower energy photons. The detector 22 includes a detector array 74 that includes an array of photodetectors to convert the light photons to electrical signals. Alternatively, the detector 22 may convert the X-ray photons directly to electrical signals. These electrical signals are converted to digital values by the detector interface circuitry 72 which provides the values to the processor 68 to be converted to imaging data and sent to the device 40 to reconstruct an image of the features within the subject 20. In one embodiment, the detector 22 may at least partially process or fully process the imaging data. Alternatively, the imaging data may be sent from the detector 22 to a server to process the imaging data.

The processor 68 is also linked to an illumination circuit 76. The detector controller 66, in response to a signal received from the device 40, may send a signal to the processor 68 to signal the illumination circuit 76 to illuminate a light 78 to indicate the detector 22 is prepared to receive an X-ray exposure in response to the signal. Indeed, in response to a signal from the device 40, the detector 22 may be turned on or awoken from an idle state. Alternatively, the detector 22 may be turned on directly or awoken from an idle state by the user (e.g., pressing an on/off button located on the detector 22).

Further, the processor is linked to a memory 80. The memory 80 may store various configuration parameters, calibration files, and detector identification data. In addition, the memory 80 may store patient information received from the device 40 to be combined with the image data to generate a DICOM compliant data file. Further, the memory 80 may store sampled data gathered during the imaging mode as well as X-ray images. As mentioned above, in some embodiments, the device 40 may conduct the image processing and incorporate a DICOM header to generate a DICOM compliant data file.

Figure 4:
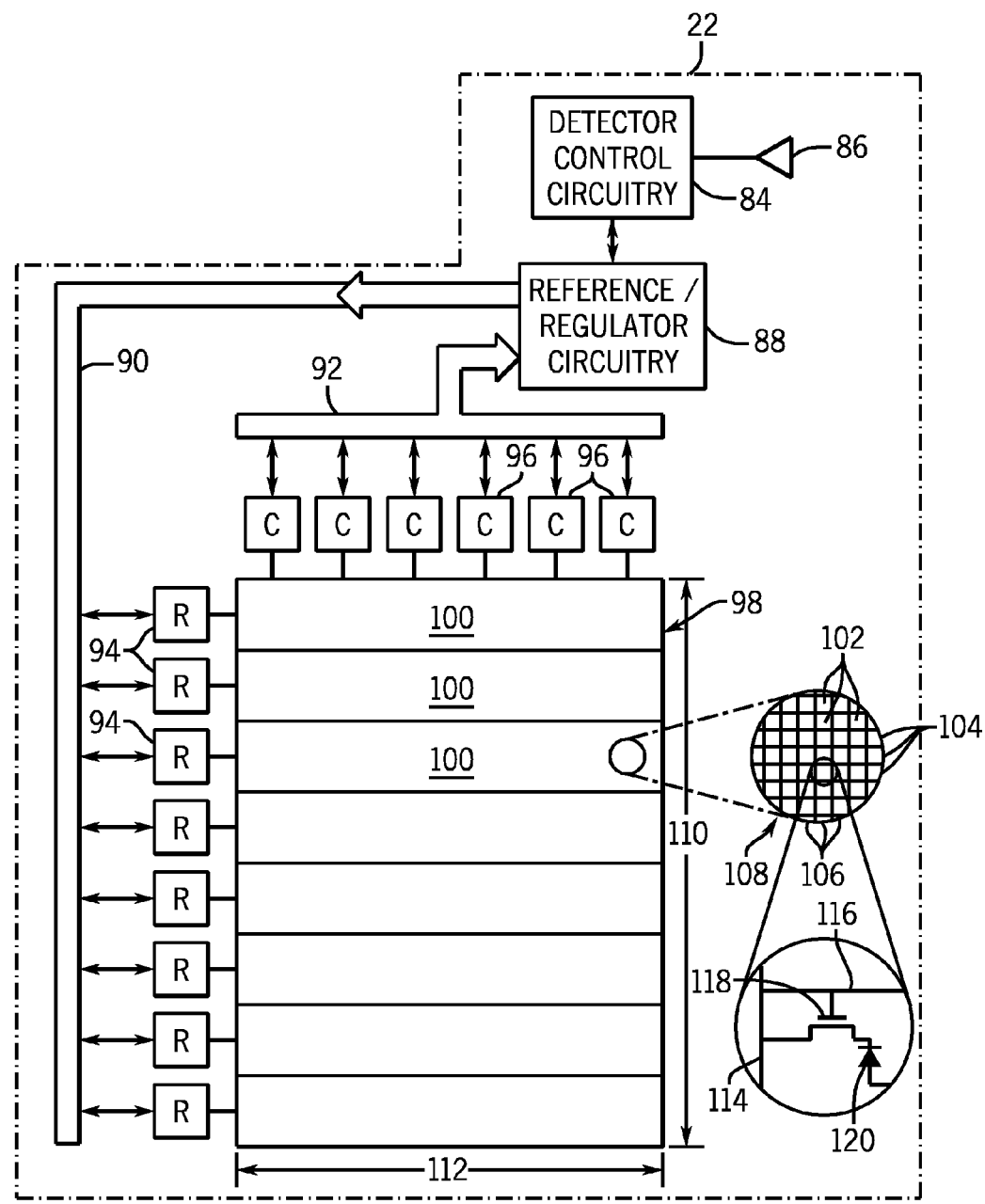
FIG. 4 is a diagrammatical representation of functional components in a detector of the system of FIGS. 1-3.

FIG. 4 is a diagrammatical representation of functional components of digital detector 22. As illustrated, detector control circuitry 84 receives DC power from a power source, represented generally at reference numeral 86. Detector control circuitry 84 is configured to originate timing and control commands for row and column electronics used to acquire image data during data acquisition phases of operation of the system. Circuitry 84 therefore transmits power and control signals to reference/regulator circuitry 88, and receives digital image pixel data from circuitry 88.

In a present embodiment, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions or picture elements of the detector surface. In certain presently contemplated, the X-ray photons may be directly converted to electrical signals. Readout electronics convert the resulting analog signals to digital values that can be processed, stored, and displayed, such as on device 40 following reconstruction of the image. In a present form, the array of photodetectors is formed of amorphous silicon. The array of photodetectors or discrete picture elements is organized in rows and columns, with each discrete picture element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual channel of the readout electronics.

As described in greater detail below, the detector control circuitry 84 is configured to sample data from the discrete picture elements prior to and during receipt of X-ray radiation. Also, the detector control circuitry 84 is configured to apply a first voltage to transistors of the discrete picture elements prior to receipt of X-ray radiation (e.g., when the detector 22 maintains idle mode). Additionally, the detector control circuitry 84 is configured to sample data from the discrete picture elements in preparation for acquisition of X-ray image data while applying a second voltage, higher than the first voltage, to transistors of the discrete picture elements not then being sampled prior to receipt of X-ray radiation. Sampled data collected prior to receipt of the X-ray radiation may be stored by the detector control circuitry 84 for use in reconstruction of a user-viewable image from the X-ray image data. Further, the detector control circuitry 84 is configured to sample data, including X-ray image data, from the discrete picture elements during receipt of X-ray radiation while applying the second voltage to the transistors of the discrete picture elements not then being sampled. Following termination of the receipt of X-ray radiation the detector control circuitry is configured to resume application of the first voltage to the transistors of the discrete picture elements.

Turning back to the embodiment illustrated in FIG. 4, by way of example, a row bus 90 includes a plurality of conductors for enabling readout from various rows of the detector 22, as well as for disabling rows and applying a charge compensation voltage to selected rows, where desired. A column bus 92 includes additional conductors for commanding readout from the columns while the rows are sequentially enabled. Row bus 90 is coupled to a series of row drivers 94, each of which commands enabling of a series of rows in the detector 22. Similarly, readout electronics 96 are coupled to column bus 92 for commanding readout of all columns of the detector.

In the illustrated embodiment, row drivers 94 and readout electronics 96 are coupled to a detector panel 98 which may be subdivided into a plurality of sections 100. Each section 100 is coupled to one of the row drivers 94, and includes a number of rows. Similarly, each column driver 96 is coupled to a series of columns. The photodiode and thin film transistor arrangement mentioned above thereby define a series of pixels or discrete picture elements 102 which are arranged in rows 104 and columns 106. The rows and columns define an image matrix 108, having a height 110 and a width 112.

As also illustrated in FIG. 4, each picture element 102 is generally defined at a row and column crossing, at which a column electrode 114 crosses a row electrode 116. As mentioned above, a thin film transistor 118 is provided at each crossing location for each picture element, as is a photodiode 120. As each row is enabled by row drivers 94, signals from each photodiode 120 may be accessed via readout electronics 96, and converted to digital signals for subsequent processing and image reconstruction. Thus, an entire row of picture elements 102 in the array is controlled simultaneously when the scan line attached to the gates of all the transistors 118 of picture elements 102 on that row is activated. Consequently, each of the picture elements 102 in that particular row is connected to a data line, through a switch, which is used by the readout electronics to restore the charge to the photodiode 120.

It should be noted that in certain systems, as the charge is restored to all the picture elements 102 in a row simultaneously by each of the associated dedicated readout channels, the readout electronics is converting the measurements from the previous row from an analog voltage to a digital value. Furthermore, the readout electronics may transfer the digital values from rows previous to the acquisition subsystem, which will perform some processing prior to displaying a diagnostic image on a monitor or writing it to film.

The circuitry used to enable the rows may be referred to in a present context as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of FETs or any particular circuit components.

Figure 5:
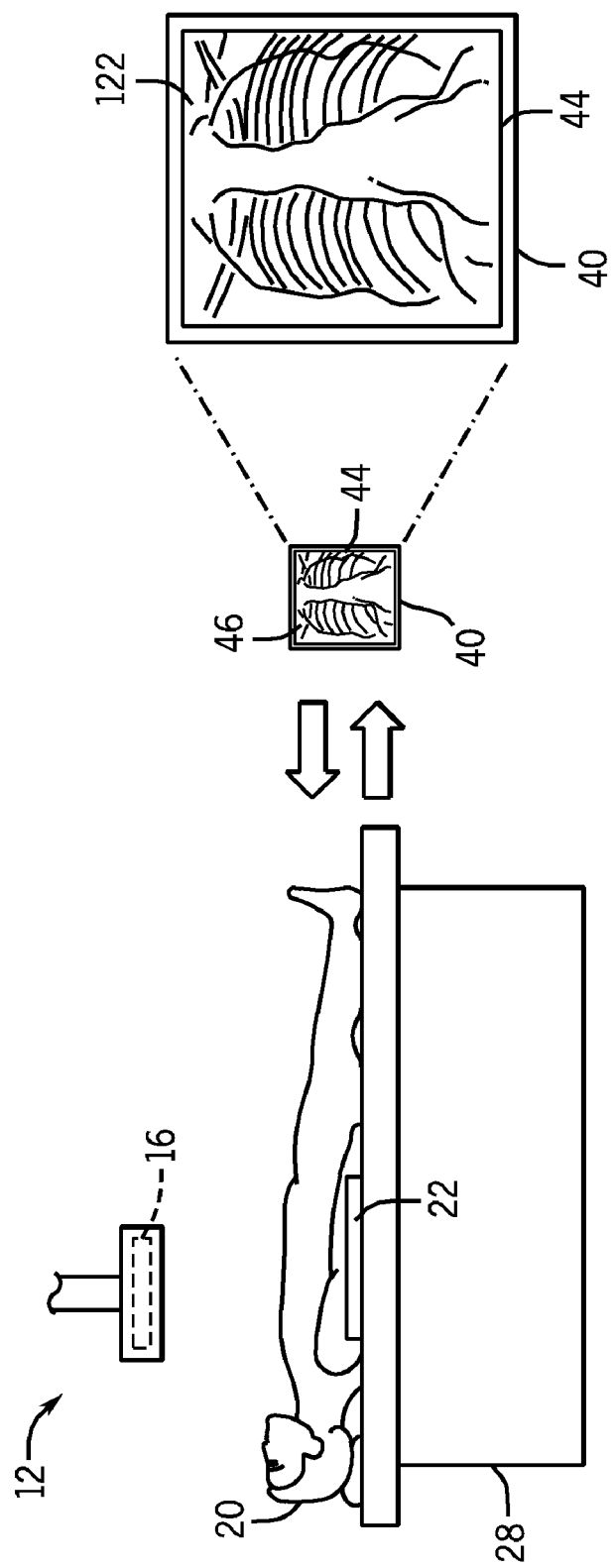
FIG. 5 is a perspective view of the two-way interaction between the detector and a portable detector control device, in accordance with aspects of the present technique.
Figure 6:
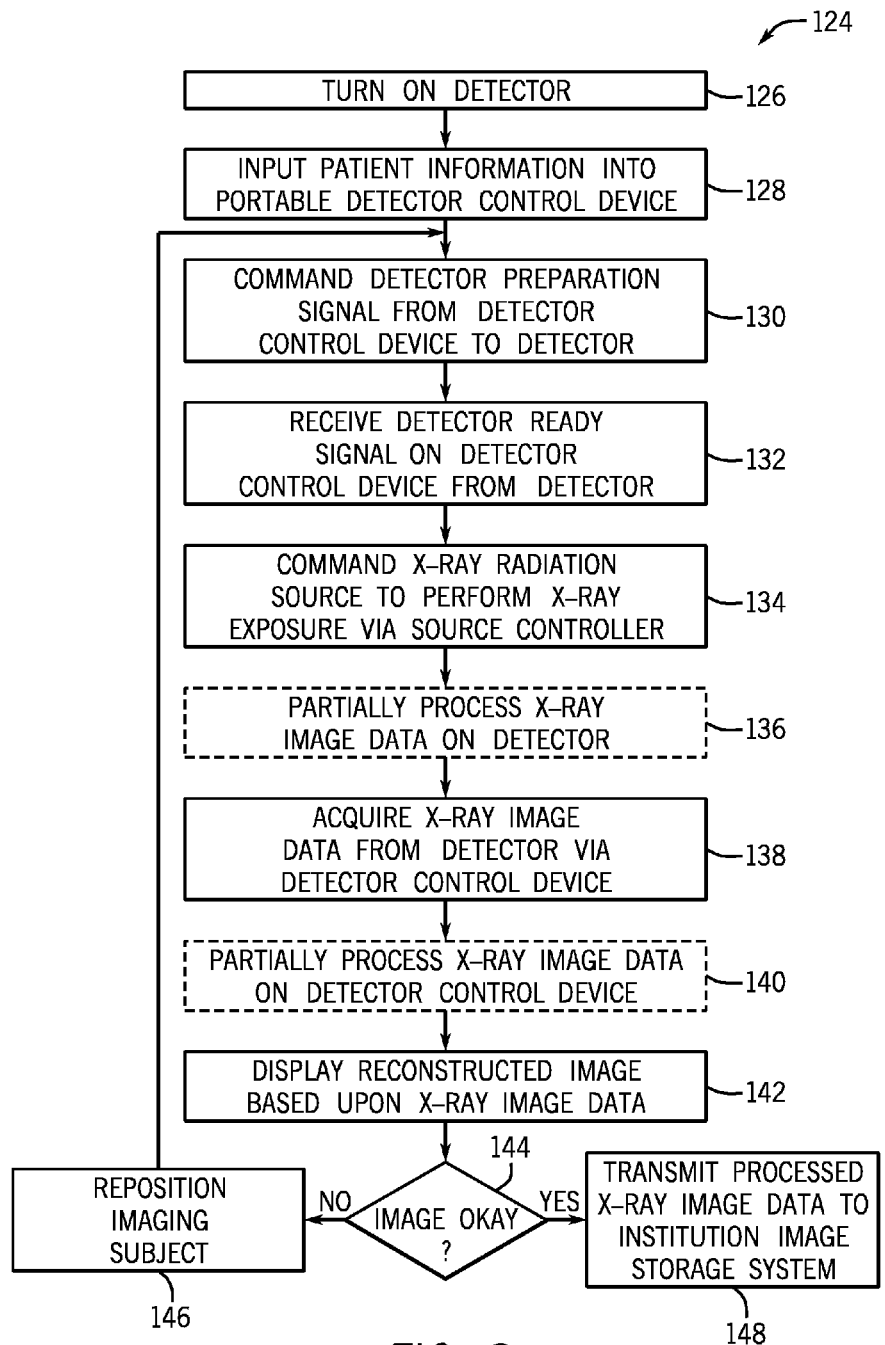
FIG. 6 is a flow diagram of a method for workflow between the detector and the portable detector control device, in accordance with aspects of the present technique.

As mentioned above, the detector 22 is without communication from the source controller 54 and, thus, is without a priori knowledge of the beginning and ending times of an exposure. In one embodiment, the detector 22 is configured to keep detecting the beginning and ending of the X-ray exposure automatically and form an X-ray image without communication with the detector control device 40. In another embodiment, the detector 22 is configured to stay in idle power mode and switch to imaging power mode after receiving a command from the detector control device 40. The detector 22 starts detecting the beginning and ending of the X-ray exposure after it is switched into full power mode. This results in a unique workflow dynamic between the X-ray system 12, detector 22, and portable detector controller device 40 as illustrated in FIGS. 5 and 6. FIG. 5 is a perspective view of the two-way interaction between the detector 22 and the portable detector control device 40. FIG. 5 illustrates the imaging system 12 with the patient 20 located on the table 28 between the X-ray source 16 and the detector 22. Here again, imaging system 12 may be a fixed or mobile system. FIG. 6 is a flow diagram of a method 124 for workflow between the detector 22 and the portable detector control device 40. To begin, the user turns on the detector 22 (block 126). The detector 22 maintains an idle mode in the on condition. As illustrated in FIG. 5, the detector 22 is located beneath the subject 20. Prior to or subsequent to turning on the detector 22, the user inputs patient information or other information (e.g., X-ray technique) related to the imaging (e.g., parameters of the image) into the device 40 (block 128). In some embodiments, the detector control device 40 may transmit the information to the detector 22, e.g., to form the DICOM compliant data file. In some other embodiments, the DICOM compliant data file is formed in the detector control device 40 so that no need to transfer the patient information to the detector 22.

The user commands a detector preparation signal from the device 40 to the detector 22 (block 130). Once the detector 22 receives the command to prepare from the device 40, the detector 22 prepares for the acquisition of X-ray image data. Specifically, the detector 22 switches from the idle mode to imaging power mode and begins scrubbing (i.e., preparing and refreshing the detector circuitry) the panel of the detector 22 to equilibrate the panel. After scrubbing, the detector 22 reads or acquires one or more offset frames prior to exposure. In particular, the detector 22 prepares for exposure by initiating sampling of data from a matrix of detector elements. After preparation, the detector 22 sends to the device 40 the detector ready signal (block 132). In one embodiment, the detector 22 may also provide a visible indication (e.g., flashing light) or an audio indication to indicate the detector is ready. In another embodiment, the detector control device 40 may provide a visible indication and/or audio indication. The user then commands the X-ray radiation source 16 to perform an X-ray exposure via the source controller 54 coupled to the source 16 (block 134).

During and after the exposure, the detector 22 samples data from the matrix of detector elements. In certain embodiments, the detector 22 at least partially processes the X-ray image data (block 136). Alternatively, the detector 22 may completely process the X-ray image data. Processing includes determining when the exposure begins and ends based upon comparison of the sampled image data generated by the detector 22. As described in greater detail below, the sampled image data may be collected from one or more frames and combined to generate the reconstructed image. The detector 22 ceases sampling after determining the end of the exposure and after sampling all of the X-ray image data from the frames. After and during the exposure, the detector control device 40 acquires X-ray image data from the detector 22 (block 138) upon which the detector 22 shifts from imaging power mode to idle mode. In certain embodiments, the device 40 at least partially processes the X-ray image data (block 140). In some embodiments, the device 40 completely processes the X-ray image data. Alternatively, the device 40 acquires completely processed X-ray image data from the detector. In other embodiments, neither the detector 22 nor the device 24 completely process the X-ray image data, but send the X-ray image data to the institution image review and storage system for subsequent processing.

As seen in FIG. 5, a reconstructed image 122 based upon the X-ray image data is displayed (block 142) on the screen 44 of the device 40. Indeed, the reconstructed image 122 may be displayed on the device 40 while the imaging subject 20 is present in a location wherein the X-ray image data is acquired. After displaying the image 122 on the device 40, the user determines whether the image is acceptable (block 144). If the image is not acceptable due to positioning issues, the imaging subject 20 may be repositioned (block 146) for a further exposure. If the image is acceptable, the user may select the interested portion of image, add the "L" and/or "R" position mark, and transmit the processed X-ray image data to the institution image review and storage system (block 148) via the detector 22 and/or device 40.

Since the detector 22 is without communication of timing signals from the source controller 54 as to performance of the exposure via the source 16, the detector samples data prior to, during, and after the exposure from one or more frames (e.g., offset and imaging frames). The length of an X-ray exposure is dependent on numerous factors such as the type of X-ray examination and the size of the imaging subject. In certain instances, the exposure may overlap frames and the sampled X-ray data from at least two imaging frames may need to be combined. However, to do this beginning and ending frames that span at least the duration of the exposure need to be determined.

FIG. 7 is a diagrammatical representation of sampling and combining X-ray image data when the exposure occurs in a single readout or sampling period. FIG. 7 illustrates multiple frames 150 obtained from sampling the matrix of detector elements. The frames 150 include offset frames 152 and 154 and imaging frames 156 and 158. The offset-corrected X-ray image is generated by combining sampled data from imaging frames 156 and 158 with sampled data (e.g., offset data from offset frame 152) gathered prior to obtaining imaging frame 156. Offset frame 152 is acquired prior to the initiation of the exposure. Offset frame 154 is acquired after the exposure ends and the frames 150 include no more image data. Neither of the offset frames 152 and 154 includes image data.

To determine the beginning and ending of the exposure and the imaging data, a row average of each frame 150 is obtained. The row average reflects the average amount of charge restored to each detector element within a row of detector elements of the detector array to fully charge the detector elements. Plot 159 from top to bottom indicates the row average of each row along the frames 150. The row average in offset frame 152 and a top portion 160 of imaging frame 156 is negligible, as indicated by portion 162 of the plot 159 since no exposure has occurred and the detector elements remain fully charged. The beginning and ending of the exposure is marked by lines 164 and 166, respectively. At line 164, 0 percent of the exposure (i.e., percent of length of total exposure) has occurred, while 100 percent of the exposure has occurred at line 166. Correspondingly, during the exposure, the row average linearly increases, indicated by portion 168 of the plot 159, as the rows are sequentially read within region 170. More specifically, the row average increases in portion 168 because each subsequent row is exposed to a greater percentage of the exposure and the detector elements within those rows require the restoration of more charge. For example, the first row read after the exposure begins may be subjected to 10 percent of exposure before being read, while the last row read may be subjected to 100 percent of the exposure before being read.

Since the exposure ended within a single sampling or reading period, both imaging frames 156 and 158 include image data indicated by the cross-hatched regions 172 and 174, respectively. Flat portion 176 of plot 159 indicates the rows in regions 178 and 180 of imaging frames 156 and 158, respectively, have been exposed to 100 percent of the exposure prior to being read. Lines 182 and 184 indicate the beginning and ending of reading rows in region 186 of frame 158 corresponding to region 170 of frame 156. As indicated by portion 188 of the plot 159, the row average linearly decreases as the rows are sequentially read within region 186. More specifically, the row average decreases in region 186 because each subsequent row was exposed to a lesser percent of the exposure after the initial reading of the rows in region 170 of reading frame 156. In other words, the row average in region 186 reflects image data from residual exposure subsequent to the last reading of the rows. For example, the first row read in region 180 of frame 158 may have been subjected to 90 percent of the exposure after the initial reading of the first row in region 170 of frame 156, while the last row read in region 180 may have been subjected to 0 percent of exposure after the initial reading of the last row in region 170 of frame 156. Portion 190 of plot 159 indicates the row average 156 in a bottom portion 192 of imaging frame 158 and the offset frame 154 is negligible since the detector elements have been recharged since last being read. As a result, by determining the row average, the beginning and ending of the exposure may be determined as well as the beginning and ending of the imaging data.

To obtain the X-ray image all of the frames 150 including image data (e.g., frames 156 and 158) are combined (i.e., added). To obtain the offset-corrected X-ray image, the total number of frames 150 used to make the X-ray image (e.g., two, frames 156 and 158) are multiplied time the calculated offset image (e.g., offset frame 152) and subtracted from the X-ray image to form the offset corrected X-ray image.

The row average may also be used when the exposure spans more than one reading or sampling period. FIG. 8 is a diagrammatical representation of sampling and combining X-ray image data when the exposure occurs over two readout or sampling periods. Similar to FIG. 7, FIG. 8 illustrates multiple frames 150 obtained from sampling the matrix of detector elements. The frames 150 include offset frames 194 and 196 and imaging frames 198, 200, and 202. Offset frame 194 is acquired prior to the initiation of the exposure. Offset frame 196 is acquired after the exposure ends and the frames 150 include no more image data. As above, neither of the offset frames 194 and 196 includes image data.

As in FIG. 7, a row average is obtained for each frame 150 in FIG. 8. Plot 204 from top to bottom indicates the row average of each row along the frames 150. The row average in offset frame 194 and a top portion 206 of imaging frame 198 is negligible, as indicated by portion 208 of the plot 204 since no exposure has occurred and the detector elements remain fully charged. The beginning and ending of the exposure is marked by lines 210 and 212, respectively. At line 210, 0 percent of the exposure has occurred, while 100 percent of the exposure has occurred at line 212. As illustrated, the exposure spans two sampling periods and, thus, two imaging frames 198 and 200. Similar to FIG. 7, FIG. 8 includes row averages that linearly increase as indicated by portion 214 of the plot 204 corresponding to regions 216 and 218 of imaging frames 198 and 200. Also, flat portion 220 of plot 204 corresponds to region 222 of imaging frame 200 and indicates those rows are exposed to 100 percent of exposure prior to being read. Portion 220 is far shorter than portion 176 of FIG. 7 because the exposure in FIG. 8 was longer and spanned more than one imaging frame meaning fewer rows of detector elements were exposed to 100 percent of the exposure prior to being read. Further, portion 224 of plot 204, corresponding to regions 226 and 228 of respective imaging frames 200 and 202, includes row averages that linearly decrease. Portions 214 and 224 of include lesser slopes than portions 168 and 188 of plot 159 in FIG. 7 due to the longer exposure in FIG. 8.

Due to the longer exposure extending two sampling periods, imaging frames 198, 200, and 202 include image data indicated by cross-hatched regions 230, 232, and 234, respectively. As above, by determining the row average, the beginning and ending of the exposure may be determined as well as the beginning and ending of the imaging data.

To obtain the X-ray image all of the frames 150 including image data (e.g., frames 198, 200, and 202) are combined (i.e., added). To obtain the offset-corrected X-ray image, the total number of frames 150 used to make the X-ray image (e.g., three, frames 198, 200, and 202) are multiplied time the calculated offset image (e.g., offset frame 194) and subtracted from the X-ray image.

Figure 9:
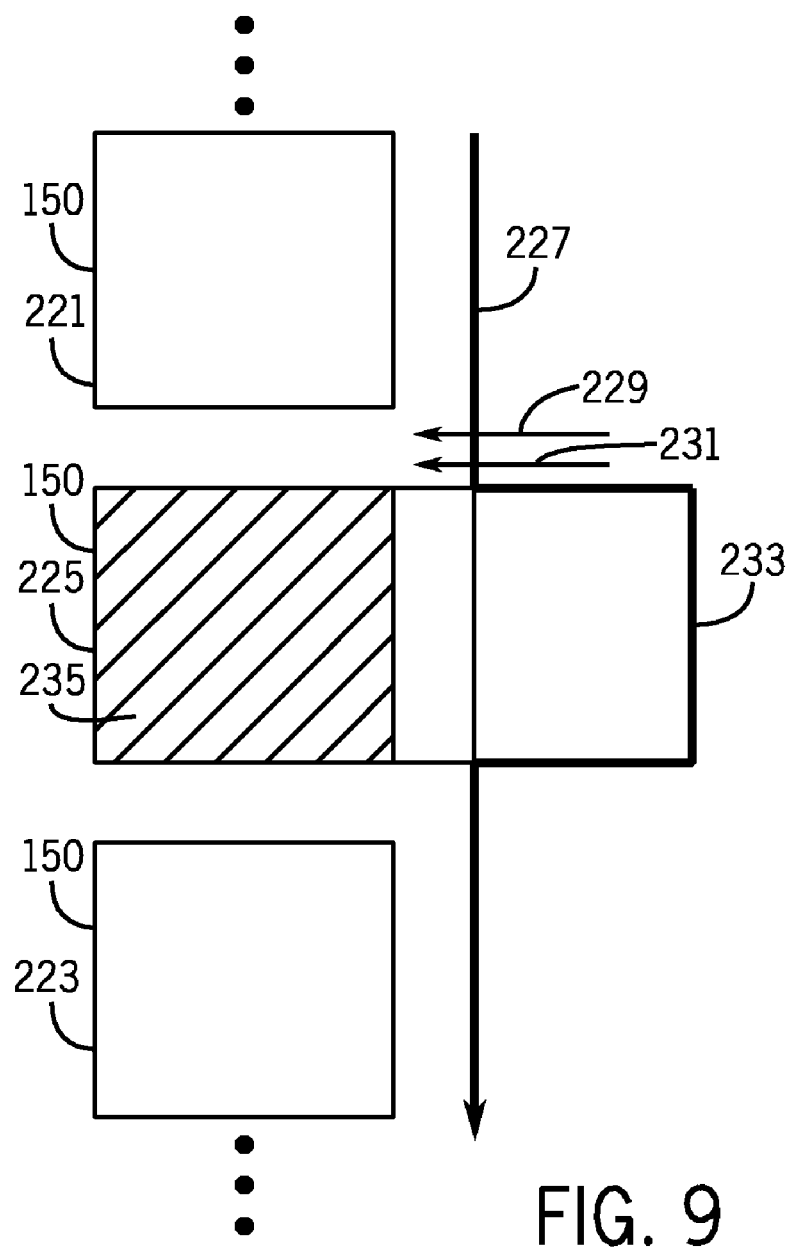
FIG. 9 is a diagrammatical representation of sampling and combining X-ray image data from one imaging frame, in accordance with aspects of the present technique.

Alternatively, the X-ray exposure may occur between readout periods. FIG. 9 is a diagrammatical representation of sampling X-ray image data when the exposure occurs after the end of one readout period but before the start of the next readout. As above, FIG. 9 illustrates multiple frames 150 obtained from sampling the matrix of detector elements. The frames 150 include offset frames 221 and 223 and imaging frame 225. Offset frame 221 is acquired prior to the initiation of the exposure. Offset frame 223 is acquired after the exposure ends and the frames 150 include no more image data. Neither of the offset frames 221 and 223 includes image data. As in FIGS. 7 and 8, a row average is obtained for each frame in FIG. 9. Plot 227 from top to bottom indicates the row average of each row along the frames 150. The row average in offset frame 221 is negligible since no exposure has occurred and the detector elements remain fully charged. The beginning and ending of the exposure is marked by lines 229 and 231, respectively. As illustrated, the exposure occurred between readouts of the frames 221 and 225. Thus, portion 233 of plot 227 indicates all of the rows are exposed to 100 percent of the exposure prior to being read. As a result, the image data indicated by cross-hatched region 235 is located with a single frame 225 and there is no need to combine the imaging frame 225 with any other frame. To obtain the offset-corrected X-ray image, the calculated offset image (e.g., offset frame 221) is subtracted from the X-ray image (e.g., frame 225).

Increases in electronic noise may occur in combining sampled X-ray image data from multiple frames (e.g., at least two imaging frames) to produce X-ray image data capable of being reconstructed into a user-viewable image. For example, assuming the X-ray image is obtained by combining three imaging frames with the same offset, for a given pixel $p_{i,j}$ where $O_{i,j}$ represents the offset value, the final value of the pixel, $\hat{p}_{i,j}$, is represented by the following formula:

$$\hat{p}_{i,j} = p_{i,j}^{(1)} + p_{i,j}^{(2)} + p_{i,j}^{(3)} - 3O_{i,j}. \tag{1}$$

The mean and variance of the electronic noise are represented by $E\{\hat{p}_{i,j}\}$ and $E\{[\hat{p}_{i,j}]^2\}$, respectively, in the following formulas where:

$$E\{\hat{p}_{i,j}\} = E\{p_{i,j}^{(1)} + p_{i,j}^{(2)} + p_{i,j}^{(3)} - 3O_{i,j}\} = 0 \tag{2}$$

and $$E\{[\hat{p}_{i,j}]^2\} = E\{[p_{i,j}^{(1)}]^2 + [p_{i,j}^{(2)}]^2 + [p_{i,j}^{(3)}]^2 [3O_{i,j}]^2\} = (3+9)\sigma^2. \tag{3}$$

Since, as shown above, the electronic noise has zero mean and the 4 values $p_{i,j}^{(1)}$, $p_{i,j}^{(2)}$, $p_{i,j}^{(3)}$, and $O_{i,j}$ are independent of each other, the electronic noise of the x-ray image by combining N offset corrected images with the same offset becomes:

$$\sqrt{(N+N^2)\sigma^2} = \sqrt{1 + 1/N} N \sigma \tag{4}$$

where $\sigma$ represents the standard deviation.

Another way of reducing the electronic noise is to use different offsets for each of the imaging frames. In that case, the electronic noise of the final image becomes:

$$\sqrt{2N}\sigma. \tag{5}$$

A further way to reduce electronic noise is to use the averaged offset for the reading frames. Assume that the offset is obtained by averaging M dark frames (i.e., offset frames). The noise of the offset is $$\frac{1}{\sqrt{M}}\sigma \tag{6}$$

and the noise of the combined image is $$\sqrt{N + N^2/M}\sigma. \tag{7}$$

Equation (7) is less than equation (5) when M>N. Thus, when the number of imaging frames combined are fewer (e.g., N=2) the averaged offset is preferred. However, when the imaging frames combined are greater, then using the same offset or separate offsets may be preferred.

FIG. 10 is a flow diagram of a method 236 for sampling and combining X-ray image data to produce X-ray image data capable of being reconstructed into a user-viewable image that incorporates the techniques described above. The method 236 includes preparing the detector 22 (block 238). Preparation of the detector 22 may include beginning sampling data (e.g., offset data) prior to and independently of initiation of an exposure. Following preparation of the detector 22, the method 236 includes performing an X-ray exposure via the X-ray radiation source 16 (block 240), where the X-ray source is responsive to the source controller 54. After initiation of the exposure, sampling of X-ray image data occurs via the detector 22 without a priori knowledge of the beginning and ending times of the X-ray exposure (i.e., without communication of timing signals from the source controller 54) (block 242) Indeed, sampling X-ray image data may occur during the X-ray exposure. The method 236 further includes determining beginning and ending frames (e.g., imaging frames) of the X-ray image data (block 244). The beginning and ending frames at least span the duration in which the exposure occurred. As mentioned above, the exposure may occur during a single imaging frame, but the X-ray image data may be on multiple imaging frames. Thus, the beginning and ending frames may contain data sampled during the duration in which the exposure occurred and data sampled outside of the duration in which the exposure occurred. In particular, the beginning and ending frames are determined by comparison of sampled data of at least the respective and ending frames. As indicated above, the beginning and ending frames are determined by identifying a changed in the sampled data values (e.g., row average) indicative of exposure to X-ray radiation.

Yet further, the method 236 includes combining the sampled X-ray image data of at least two imaging frames, where at least one of the frames spans the duration in which the exposure occurred, to produce X-ray image data capable of being reconstructed into a user-viewable image (block 246). As mentioned above, X-ray image data capable of being reconstructed into a user-viewable image may be produced by generating offset corrected image data based upon data sampled from the at least two imaging frames. For example, the offset corrected image data is generated by combining sampled data prior to a beginning imaging frame with data sampled from the at least two imaging frames as described above. Further, combining the sampled X-ray image data of the at least two imaging frames includes selecting a combination method based upon a noise parameter. In other words, as described above, the calculation of the noise will depend on the number of imaging frames and offset frames (i.e., offset frames) sampled prior to and during the occurrence of the exposure to select the proper equation from those noted above to reduce electronic noise when combining the sampled data from more than one frame.

The above techniques are illustrated in FIG. 11, a diagrammatical representation of workflow during an acquisition sequence in which both image data and offset data are acquired for producing user-viewable images. FIG. 11 includes an acquisition sequence 248 of the detector 22 corresponding to the interaction between the detector 22, portable detector control device 40, the operator or user 38, and the X-ray source 16. The detector 22, device 40, and operation of the source 16 are as described above. While the detector 22 is in idle mode, represented by region 250 of the sequence 248, the operator 38 configures the source 16 as indicated by arrow 252. Configuring the source 16 may include setting exposure parameters and the type of exposure. Also, while the detector 22 remains in idle mode, the operator may position the imaging subject and the source 16. Further, the operator 38 enters instructions into device 40, as indicated by arrow 254, and sends instructions 256 to the detector 22 to prepare for exposure.

Upon receiving the instructions to prepare for acquisition of X-ray image data, the detector 22 enters imaging power mode 258. The detector 22 begins by scrubbing the panel, as indicated by region 260 of the acquisition sequence 248, to equilibrate the circuitry on the panel. Then, the detector 22 reads one or more offset frames from the panel (e.g., region 262), upon which the detector 22 sends a detector ready signal 264 to the device 40. In one embodiment, the device 40 provides a visual indication to indicate the ready state of the detector 22. In another embodiment, the device 40 provides an audio indication. In a further embodiment, the device 40 provides both video and audio indications. In a yet further embodiment, the detector 22 provides a visual indication (e.g., flashing LED) to indicate the ready state of the detector 22. In another embodiment, the detector 22 provides an audio indication. Yet in another embodiment, the detector 22 provides both video and audio indications. The operator 38 receives the ready signal on the device 40, as indicated by arrow 266. Once the detector 22 is ready, the detector 22 begins continuously sampling or reading frames as indicated by region 268 of the acquisition sequence 248 to detect an exposure. At any time, the operator may initiate the exposure, as indicated by arrow 270, from the source 16. Upon initiation of the exposure, the detector 22 receives the X-ray radiation 272 from the source 16. The detector 22 samples the frames to determine the beginning and ending frames that span the exposure (e.g., frames 274 and 276). After termination of the exposure, the detector 22 may process the acquired image data and send a preview of a reconstructed image, indicated by arrow 278, to the device 40 for viewing by the operator 38. Alternatively, the data may be sent to the device 40 for further processing and the generation of the reconstructed image. After the exposure ends, the detector 22 reverts back to idle mode as indicated by region 280 of the acquisition sequence 248.

As mentioned above, the detector 22 shifts from an idle mode to an imaging power mode. In the imaging power mode, the detector 22 continuously reads the panel, since the detector 22 lacks a priori knowledge (or data) of when the exposure may occur. Thus, reading or sampling of data from the panel occurs during the exposure. Transistors (e.g., FETs) of discrete picture elements then being sampled are in a conducting state when the rows are enabled for readout. However, leakage (e.g., FET leakage) may occur from those transistors of discrete picture elements not then being sampled (i.e., transistors are in a non-conducting state when the rows are not enabled for readout). Increasing the voltage ($V_{off}$) to maintain the transistors not then being sampled in a non-conductive state may reduce FET leakage. However, reduction of the leakage may not persist if the transistors are biased for a while due to bias age.

Figure 12:
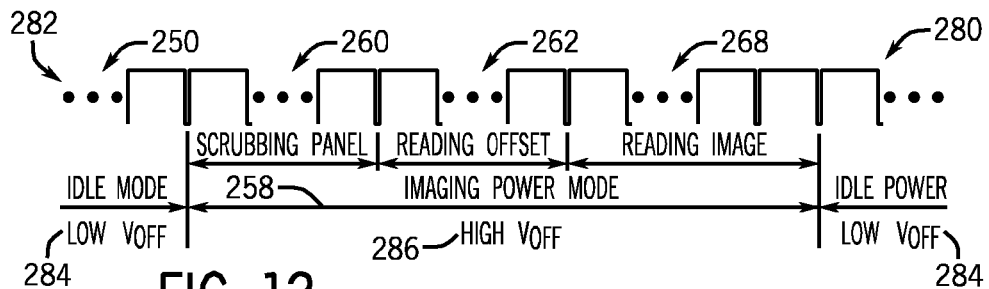
FIG. 12 is a diagrammatical representation of an acquisition sequence in which different voltages are applied to reduce transistor leakage while sampling image data, in accordance with aspects of the present technique.
Figure 13:
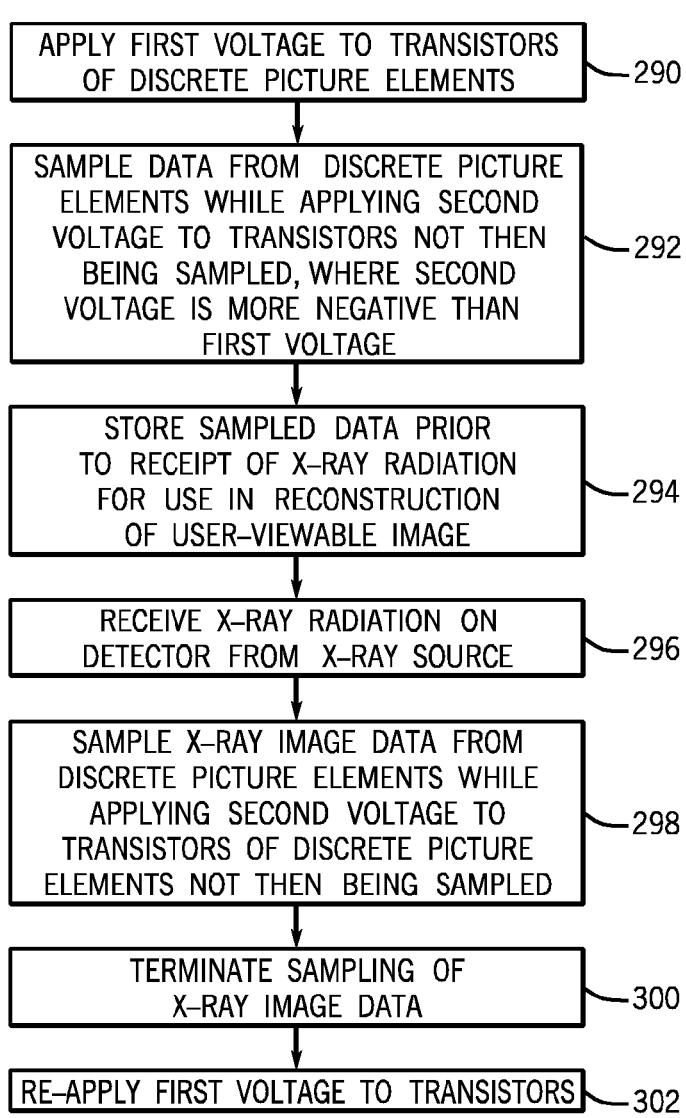
FIG. 13 is a flow diagram of a method for sampling data from the detector prior to and after an X-ray exposure while applying different voltages to reduce transistor leakage, in accordance with aspects of the present technique.

FIGS. 12 and 13 illustrate embodiments of techniques to overcome these issues. FIG. 12 is a diagrammatical representation of an acquisition sequence 282 in which different voltages are applied to reduce transistor leakage while sampling image data, particularly during exposure. The acquisition signal 282 of FIG. 12 is the same as acquisition signal 248 described in FIG. 11. The acquisition signal 282 includes regions 250 and 280 where the detector 22 maintains an idle mode. In addition, the acquisition signal 282 includes regions where the detector 22 scrubs the panel (e.g., region 260) and periods of sampling or reading the panel (e.g., regions 262 and 268). The detector 22 applies a first voltage 284 (e.g., less negative $V_{off}$) to the transistors of the discrete picture elements when the detector 22 maintains an idle mode (e.g., regions 250 and 280). Thus, the detector 22 applies the first voltage 284 to the transistors of the discrete picture elements prior to receipt of X-ray radiation (e.g., region 250). The detector 22 applies a second voltage 286 (e.g., more negative $V_{off}$) to the transistors of the discrete picture elements not then being sampled when the detector 22 shifts to imaging power mode 258 (e.g., regions 260, 262, and 268) and begins sampling data from the discrete picture elements. In one embodiment, the first voltage 284 may be applied, instead of the second voltage 286, while scrubbing the panel (i.e., region 260). The application of the second voltage 286 to the transistors of the discrete picture elements not then being sampled also occurs during receipt of X-ray radiation by the detector 22. Upon termination of sampling X-ray data from the discrete picture elements (e.g., region 280), the detector 22 reapplies the first voltage 284 to the transistors of the discrete picture elements after termination of the receipt of X-ray radiation by the detector 22.

The second voltage 286 is more negative than the first voltage 284. The second voltage 286 may be at least approximately 1.3 times the first voltage 284. For example, the first voltage 284 may be equal to or less negative than approximately −11 volts. The second voltage 286 may be equal to or more negative than approximately −15 volts. The first and second voltages 284 and 286 maintain the transistors in a non-conductive state. By maintaining the second voltage 286 only during the imaging power mode 258 and shifting to the first voltage 284 in idle mode (e.g., regions 250 and 280), the transistor leakage may be reduced while also avoiding bias age.

FIG. 13 is a flow diagram of a method 288 for sampling data from the detector prior to and after an X-ray exposure while applying different voltages to reduce transistor leakage. The method 288 includes applying the first voltage 284 to transistors of the discrete picture elements (e.g., when detector 22 maintains idle mode) (block 290). While preparing for the acquisition of X-ray image data, the method 288 includes sampling data from the discrete picture elements while applying the second voltage 286 to the transistors of the discrete picture elements not then being sampled, where the second voltage 286 is more negative than the first voltage 284 (block 292). Upon sampling data while applying the second voltage 286, the detector 22 may store sampled data prior to receipt of the X-ray radiation for use in reconstruction of a user-viewable image from the X-ray image data (block 294). Also, the method 288 includes receiving X-ray radiation on the detector 22 from the X-ray source 16 (block 296). After exposure, sampling of X-ray image data from the discrete picture elements occurs while applying the second voltage 286 to the transistors of the discrete picture elements not then being sampled (block 298). Sampling of data from the discrete picture elements also occurs during receipt of X-ray radiation, while applying the second voltage 286 to the transistors of the discrete picture elements not then being sampled. After termination of receipt of X-ray radiation, the detector 22 terminates sampling of X-ray image data from the discrete picture elements (block 300) and re-applies the first voltage 284 to the transistors of the discrete picture elements (block 302), for example, during the transition to idle mode. As mentioned above, transistor leakage may be reduced while also avoiding bias age by maintaining the second voltage 286 only during the imaging power mode and shifting to the first voltage 284 in idle mode.

Technical effects of the embodiments include providing methods and systems to allow for the retrofitting of conventional X-ray systems by replacing cassettes with a digital X-ray detector. In retrofitting the X-ray systems, the digital X-ray detector does not communicate with the X-ray imaging system. Instead, the detector communicates with a portable detector control device to receive instructions. Since the detector does not communicate with the X-ray system, the detector lacks data indicating the timing signals for an X-ray exposure. Thus, the detector in preparation for and during an exposure may continuously read the panel of the detector. The detector may include techniques to determine the beginning and ending of the exposure and imaging data, gather and combine X-ray image data from multiple frames, while reducing factors that may adversely affect the quality of the image (e.g., electrical noise and transistor leakage).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging method, comprising:
performing an X-ray exposure via an X-ray radiation source responsive to a source controller;
sampling X-ray image data via a digital detector without communication of timing signals from the source controller;
combining the sampled X-ray image data of at least one imaging frame or two or more imaging frames with at least one of the frames spanning a duration in which the exposure occurred, to produce X-ray image data capable of being reconstructed into a user-viewable image.

2. The method of claim 1, comprising generating an image frame where the X-ray exposure occurs between image reading of two consecutive frames.

3. The method of claim 1, comprising determining beginning and ending frames that span at least the duration in which the exposure occurred.

4. The method of claim 3, wherein each of the beginning and ending frames contain data sampled during the duration in which the exposure occurred and data sampled outside of the duration in which the exposure occurred.

5. The method of claim 3, wherein the beginning and ending frames are determined by comparison of sampled data of at least the respective beginning and ending frames.

6. The method of claim 5, wherein the beginning and ending frames are determined by identifying a change in sampled data values indicative of exposure to X-ray radiation.

7. The method of claim 1, comprising preparing the detector by sampling data prior to the exposure.

8. The method of claim 7, wherein preparing the detector comprises beginning sampling of detector data prior to and independently of initiation of the exposure.

9. The method of claim 1, comprising producing X-ray image data capable of being reconstructed into a user-viewable image by generating offset corrected image data based upon data sampled from the at least one imaging frame.

10. The method of claim 9, wherein the offset corrected image data is generated by combining sampled data prior to a beginning image frame with data sampled from the at least one imaging frames.

11. The method of claim 1, wherein combining the sampled X-ray image data of the two or more imaging frames comprises selecting a combination method based upon a noise parameter.

12. The method of claim 11, wherein the noise parameter is based upon a number of imaging frames that at least span the duration in which the exposure occurred, and a number of imaging frames sampled prior to initiation of the exposure.

13. An X-ray imaging method, comprising:
performing an X-ray exposure via an X-ray radiation source;
sampling X-ray image data via a digital detector without a priori knowledge of beginning and ending times of the X-ray exposure;
determining beginning and ending frames of the X-ray image data; and
combining the sampled X-ray image data of at least one imaging frame or two or more imaging frames with at least one of the frames spanning a duration in which the exposure occurred, to produce X-ray image data capable of being reconstructed into a user-viewable image.

14. The method of claim 13, comprising sampling X-ray image data during the X-ray exposure.

15. The method of claim 13, wherein the beginning and ending frames contain data sampled during the duration in which the exposure occurred and data sampled outside of the duration in which the exposure occurred.

16. The method of claim 13, wherein the beginning and ending frames are determined by comparison of sampled data of at least the respective beginning and ending frames.

17. The method of claim 16, wherein the beginning and ending frames are determined by identifying a change in sampled data values indicative of exposure to X-ray radiation.

18. The method of claim 13, comprising preparing the detector by sampling data prior to the exposure.

19. The method of claim 18, wherein preparing the detector comprises beginning sampling of detector data prior to and independently of initiation of the exposure.

20. The method of claim 13, comprising producing X-ray image data capable of being reconstructed into a user-viewable image by generating offset corrected image data based upon data sampled from the at least one imaging frame.

21. The method of claim 20, wherein the offset corrected image data is generated by combining sampled data prior to the beginning image frame with data sampled from the at least one imaging frame.

22. The method of claim 13, wherein combining the sampled X-ray image data of the two or more imaging frames comprises selecting a combination method based upon a noise parameter.

23. The method of claim 22, wherein the noise parameter is based upon a number of imaging frames that at least span the duration in which the exposure occurred, and a number of imaging frames sampled prior to initiation of the exposure.

24. An X-ray imaging system comprising:
an X-ray radiation source;
a source controller coupled to the source and configured to command X-ray emission of X-rays for image exposures;
a digital X-ray detector configured to sample X-ray image data without communication from the source controller; and
a portable detector control device configured to communicate instructions to the detector for acquisition of the X-ray image data and to receive the X-ray image data from the detector for processing, image reconstruction, and image preview;
wherein at least one of the detector, the portable detector control device, and a processing system in communication with the detector and/or the portable detector control device is configured to combine the sampled X-ray image data of at least one imaging frame or two or more imaging frames with at least one of the frames spanning a duration in which the exposure occurred, to produce X-ray image data capable of being reconstructed into a user-viewable image.

25. The system of claim 24, wherein producing X-ray image data capable of being reconstructed into a user-viewable image comprises generating offset corrected image data based upon data sampled from the at least one imaging frame.

26. The system of claim 25, wherein the offset corrected image data is generated by combining sampled data prior to a beginning frame with data sampled from the at least one imaging frame.

27. A digital X-ray detector comprising:
circuitry configured to sample X-ray image data without communication from timing signals from a source controller, wherein the source controller is configured to command X-ray emissions of X-ray from an X-ray radiation source for image exposures, and to combine the sampled data of at least one imaging frame with at least one of the frames spanning a duration in which an X-ray exposure occurred to produce X-ray image data capable of being reconstructed into a user-viewable image.

28. The digital X-ray detector of claim 27, wherein the circuitry is configured to combine the sampled data of two or more imaging frames with at least one of the frames spanning the duration in which the exposure occurred to produce X-ray image data capable of being reconstructed into the user-viewable image.

29. The digital X-ray detector of claim 28, wherein combining the sampled X-ray image data of the two or more imaging frames comprises selecting a combination method based upon a noise parameter.

30. The digital X-ray detector of claim 29, wherein the noise paramater is based upon a number of imaging frames that at least span the duration in which the exposure occurred, and a number of imaging frames sampled prior to initiation of the exposure.

31. The digital X-ray detector of claim 27, wherein the circuitry is configured to generate an image frame where the X-ray exposure occurs between image reading of two consecutive frames.

32. The digital X-ray detector of claim 27, wherein the circuitry is configured to determine beginning and ending frames that span at least the duration in which the exposure occurred.

33. The digital X-ray detector of claim 32, wherein each of the beginning and ending frames contain data sampled during the duration in which the exposure occurred and data sampled outside the duration in which the exposure occurred.

34. The digital X-ray detector of claim 32, wherein the circuitry is configured to determine the beginning and ending frames by comparing sampled data of at least the respective beginning and ending frames.

35. The digital X-ray detector of claim 34, wherein the circuitry is configured to determine the beginning and ending frames by indentifying a change in the sampled data values indicative of exposure to X-ray radiation.

36. The digital X-ray detector of claim 27, wherein the circuitry is configured to prepare the detector by sampling data prior to the exposure.

37. The digital X-ray detector of claim 36, wherein the circuitry is configured to begin sampling of detector data prior to and independently of initiation of the exposure.

38. The digital X-ray detector of claim 27, wherein the circuitry is configured to produce X-ray image data capable of being reconstructed into a user-viewable image by generating offset corrected image data based upon data sampled from the at last one imaging frame.

39. The digital X-ray detector of claim 38, wherein the offset corrected image data is generated by combining sampled data prior to a beginning image frame with data sampled from the at least one imaging frame.

* * * * *